(12) United States Patent
Chung

(10) Patent No.: US 11,339,424 B2
(45) Date of Patent: May 24, 2022

(54) METHOD FOR AMPLIFICATION AND QUANTITATION OF SMALL AMOUNT OF MUTATION USING MOLECULAR BARCODE AND BLOCKING OLIGONUCLEOTIDE

(71) Applicant: DXOME CO., LTD., Seoul (KR)

(72) Inventor: Jun Hyuk Chung, Yongin-si (KR)

(73) Assignee: DXOME CO., LTD., Seoul (KR)

( * ) Notice: Subject to any disclaimer, the term of this patent is extended or adjusted under 35 U.S.C. 154(b) by 64 days.

(21) Appl. No.: 16/644,712

(22) PCT Filed: Sep. 6, 2018

(86) PCT No.: PCT/KR2018/010441
§ 371 (c)(1),
(2) Date: Jul. 7, 2020

(87) PCT Pub. No.: WO2019/050303
PCT Pub. Date: Mar. 14, 2019

(65) Prior Publication Data
US 2020/0332355 A1    Oct. 22, 2020

(30) Foreign Application Priority Data

Sep. 6, 2017 (KR) ........................ 10-2017-0113828

(51) Int. Cl.
*C12Q 1/6851* (2018.01)
*C12Q 1/6832* (2018.01)
*C12N 15/10* (2006.01)

(52) U.S. Cl.
CPC ....... *C12Q 1/6851* (2013.01); *C12N 15/1093* (2013.01); *C12Q 1/6832* (2013.01); *C12Q 2527/101* (2013.01); *C12Q 2531/113* (2013.01); *C12Q 2600/156* (2013.01)

(58) Field of Classification Search
CPC ........ C12Q 2525/191; C12Q 2535/119; C12Q 1/6869; C12Q 2531/113; C12Q 1/6851; C12Q 2525/113; C12Q 1/6832; C12Q 2527/101; C12Q 2535/122; C12Q 2563/179; C12Q 2600/156; C12N 15/1093
See application file for complete search history.

(56) References Cited

U.S. PATENT DOCUMENTS 10,246,702 B1 * 4/2019 Richard ............ C12N 15/1065
2010/0009355 A1   1/2010 Kolodney
(Continued)

FOREIGN PATENT DOCUMENTS

KR   1020160141680 A   12/2016
WO      2016172265 A1   10/2016
WO   WO-2016172265 A1 * 10/2016 ........... C12Q 1/6858

OTHER PUBLICATIONS

International Search Report issued in PCT/KR2018/010441, dated Dec. 27, 2018, 2 pages provided.
(Continued)

*Primary Examiner* — Young J Kim
(74) *Attorney, Agent, or Firm* — Hamre, Schumann, Mueller & Larson, P.C.

(57) ABSTRACT

The present disclosure relates to a method for amplification and quantitation of a small amount of mutation using a molecular barcode and a blocking oligonucleotide.

8 Claims, 7 Drawing Sheets

Specification includes a Sequence Listing.

1) STRUCTURE OF FASTQ DATA FILE SEQUENCE

2) REMOVAL OF ADAPTOR SEQUENCE, MOLECULAR BARCODE SEQUENCE AND FIXED SEQUENCE

3) RE-LIGATION OF MOLECULAR BARCODE SEQUENCE

(56) References Cited

U.S. PATENT DOCUMENTS

2015/0051116 A1     2/2015   Kim
2016/0257993 A1*   9/2016   Fu ........................ C12Q 1/6844

OTHER PUBLICATIONS

Hidetoshi Urakawa et al., "Optimization of Single-Base-Pair Mismatch Discrimination in Oligonucleotide Microarrays", Applied and Environmental Microbiology vol. 69, No. 5, May 2003, p. 2848-2856.

Qing Wang et al., "Targeted sequencing of both DNA strands barcoded and captured individually by RNA probes to identify genome-wide ultra-rare mutations", Scientific Reports, Jun. 13, 2017, 14 pages provided; cited in ISR.

Michael W. Schmitt et al., "Detection of ultra-rare mutations by next-generation sequencing", PNAS, Sep. 4, 2012, vol. 109, No. 36, 6 pages provided; cited in ISR.

* cited by examiner

METHOD FOR AMPLIFICATION AND QUANTITATION OF SMALL AMOUNT OF MUTATION USING MOLECULAR BARCODE AND BLOCKING OLIGONUCLEOTIDE

TECHNICAL FIELD

The present disclosure relates to a method for amplification and quantitation of a small amount of mutation using a molecular barcode and a blocking oligonucleotide.

BACKGROUND

PCR clamping is a method for selectively amplifying DNA with mutations by blocking normal DNA and may include, for example, locked nucleic acid (LNA) method, peptide nucleic add (PNA) method and mutant-enrichment with 3'-modified oligonucleotide (MEMO) method. These methods can improve the sensitivity and specificity of DNA with mutations detection by increasing the amplification efficiency of the DNA with mutations.

However, these methods can only qualitatively detect mutation DNA, but cannot quantitatively measure the ratio of DNA with mutations.

DISCLOSURE OF THE INVENTION

Problems to be Solved by the Invention

The present disclosure is conceived to provide a method for amplification and quantitation of a small amount of mutation using a molecular barcode and a blocking oligonucleotide.

However, problems to be solved by the present disclosure are not limited to the above-described problems. Although not described herein, other problems to be solved by the present disclosure can be clearly understood by a person with ordinary skill in the art from the following description.

Means for Solving the Problems

A first aspect of the present disclosure provides a method for producing a library for next-generation sequencing, including: ligating adaptors to both ends of a target double-stranded DNA fragment; providing a pair of primers for amplifying the DNA fragment; producing an amplification product of the DNA fragment containing a molecular barcode by amplifying the adaptor-ligated DNA fragment using the pair of primers; capturing a specific DNA sequence to be selected from the amplification product of the DNA fragment containing the molecular barcode by hybridization with a nucleic acid probe and a blocking oligonucleotide; and amplifying the captured product using a common primer sequence, and each of the paired primers includes i) an adaptor-complementary sequence having a nucleotide sequence complementary to the adaptors, ii) a sample-unique sequence having the same nucleotide sequence for each DNA fragment, iii) a molecular barcode having a nucleotide sequence unique to each DNA fragment, and iv) a fixed sequence for distinguishing the molecular barcode and a DNA sequence, and the blocking oligonucleotide has a sequence complementary to a wild-type of specific DNA sequence to be selected from DNA fragments.

A second aspect of the present disclosure provides a method for detecting a small amount of mutation sequence using next-generation sequencing, including: performing next-generation sequencing of a library produced by the method according to the first aspect of the present disclosure; aligning, in a reference sequence, the library from which an adaptor-complementary sequence and a molecular barcode sequence are removed; re-ligating a molecular barcode to the aligned sequence; and performing sequencing of the re-ligated sequence.

Effects of the Invention

According to an embodiment of the present disclosure, a small amount of DNA with mutations can be analyzed more accurately, which makes it possible to detect a small amount of mutation that has been removed by error determination according to the conventional next-generation sequencing and quantitatively measure the ratio of DNA with mutations.

BEST MODE FOR CARRYING OUT THE INVENTION

Figure 1:
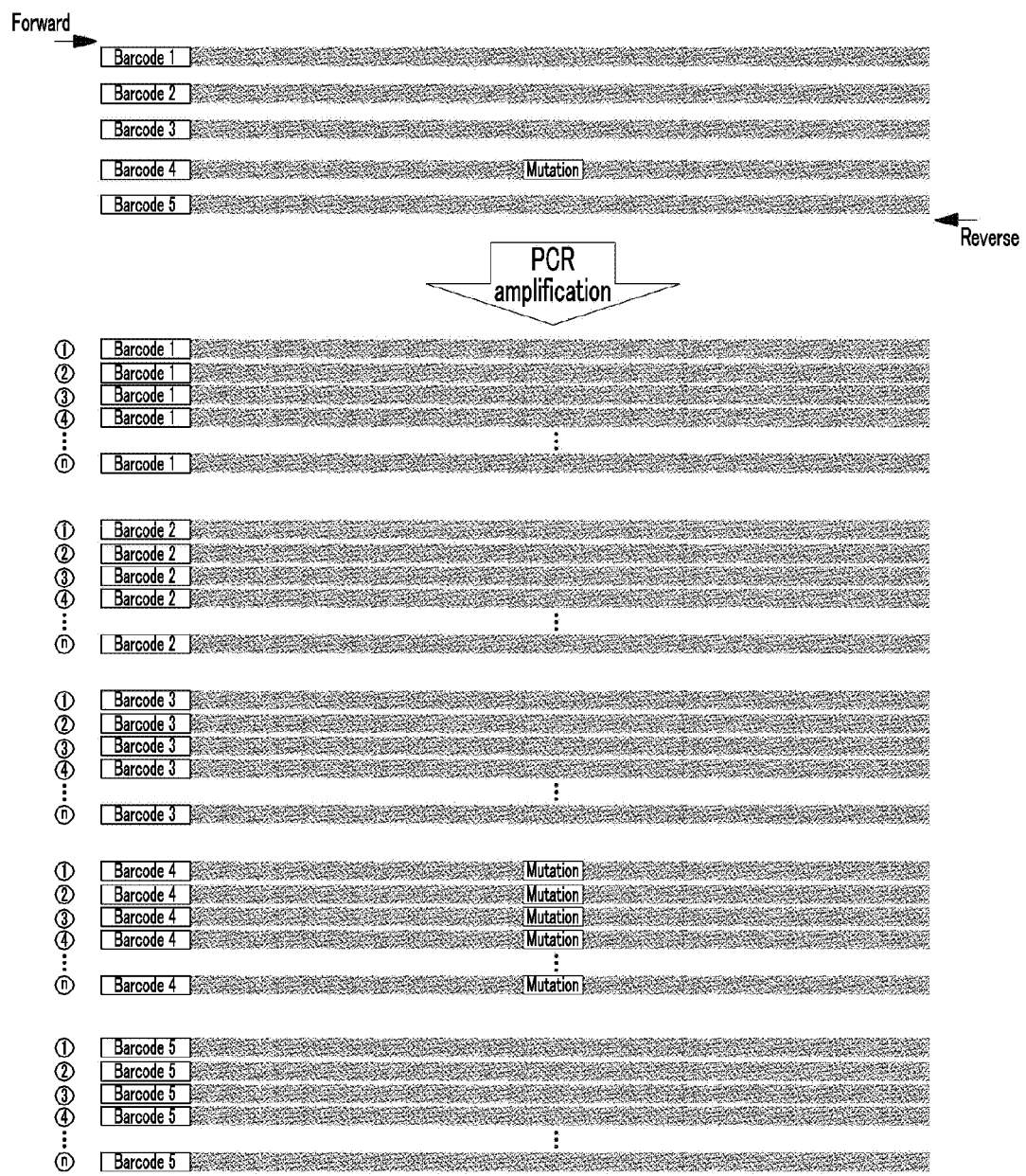
FIG. 1 is a schematic diagram illustrating the principle of a molecular barcode according to an embodiment of the present disclosure.

Hereafter, examples will be described in detail with reference to the accompanying drawings so that the present disclosure may be readily implemented by those skilled in the art. However, it is to be noted that the present disclosure is not limited to the examples but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected to" another element and an element being "electronically connected to" another element via another element.

Through the whole document, the term "on" that is used to designate a position of one element with respect to another element includes both a case that the one element is adjacent to the other element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereinafter, embodiments and examples of the present disclosure will be described in detail with reference to the accompanying drawings. However, the present disclosure may not be limited to the following embodiments, examples, and drawings.

A first aspect of the present disclosure provides a method for producing a library for next-generation sequencing, including ligating adaptors to both ends of a target double-stranded DNA fragment; providing a pair of primers for amplifying the DNA fragment; producing an amplification product of the DNA fragment containing a molecular barcode by amplifying the adaptor-ligated DNA fragment using the pair of primers; capturing a specific DNA sequence to be selected from the amplification product of the DNA fragment containing the molecular barcode by hybridization with a nucleic acid probe and a blocking oligonucleotide; and amplifying the captured product using a common primer sequence, and each of the paired primers includes i) an adaptor-complementary sequence having a nucleotide sequence complementary to the adaptors, ii) a sample-unique sequence having the same nucleotide sequence for each DNA fragment, iii) a molecular barcode having a nucleotide sequence unique to each DNA fragment, and iv) a fixed sequence for distinguishing the molecular barcode and a DNA sequence, and the blocking oligonucleotide has a sequence complementary to a wild-type of specific DNA sequence to be selected from DNA fragments.

In an embodiment of the present disclosure, the target double-stranded DNA may naturally occur or may be synthetically prepared. For example, the naturally occurring DNA may be cell-derived DNA or cell-free DNA, but may not be limited thereto.

In an embodiment of the present disclosure, the target double-stranded DNA fragment may be prepared by fragmenting a naturally occurring sequence to a predetermined size, but may not be limited thereto. For example, the fragmentation can be performed using ultrasonic waves, heat, enzymes, and the like, and the enzymes may include transposases, such as Tn5 transposase or Tn3 transposase, integrases, and recombinases, but may not be limited thereto.

In an embodiment of the present disclosure, the method may include an end-repair process for making the both ends of the target double-stranded DNA fragment blunt-ended. Further, the method may include an adenosine-tailing (A-tailing) process for binding an adenosine base to the 3'-end to bind adaptors to the both ends of the target double-stranded DNA fragment in a predetermined direction. The above-described processes may be performed using, for example, T4 DNA polymerase and Klenow fragment, but may not be limited thereto.

In an embodiment of the present disclosure, the method may further include a process for phosphorylating both 5'-ends of the target double-stranded DNA fragment, but may not be limited thereto. For example, the phosphorylation may be performed using an enzyme such as T4 polynucleotide phosphorylase.

In an embodiment of the present disclosure, the method may further include a process for purifying the target double-stranded DNA fragment before and after the end-repair process and the A-tailing process, but may not be limited thereto.

In an embodiment of the present disclosure, the adaptors may be ligated to the both ends of the target double-stranded DNA fragment using a ligase. For example, the ligase may include a T4 DNA ligase, a T7 DNA ligase, or a ligase capable of temperature cycling, but may not be limited thereto.

In an embodiment of the present disclosure, the adaptors ligated to the both ends of the target double-stranded DNA fragment may have a Y-shape or U-shape. For example, if the adaptors have a U-shape, the method may further include cleaving the inner region of the ligated adaptor using an enzyme. For example, the U-shaped adaptor may be cleaved into an adaptor having a Y-shaped end using an enzyme such as uracil-specific excision reagent (USER), but may not be limited thereto.

In an embodiment of the present disclosure, the pair of primers may be provided to amplify the DNA fragment. Each of the paired primers may include i) an adaptor-complementary sequence having a nucleotide sequence complementary to the adaptors, ii) a sample-unique sequence having the same nucleotide sequence for each DNA fragment, iii) a molecular barcode having a nucleotide sequence unique to each DNA fragment, and iv) a fixed sequence for distinguishing the molecular barcode and a DNA sequence.

In an embodiment of the present disclosure, the molecular barcode is a barcode sequence to be uniquely ligated to each DNA fragment and configured to distinguish different DNA fragments from each other. The molecular barcode has a nucleotide sequence unique to each single-stranded DNA fragment present in a sample and configured to distinguish DNA fragments present in a sample. For example, the molecular barcode may consist of from 4 to 10 nucleotides, from 4 to 8 nucleotides, from 4 to 6 nucleotides, from 6 to 10 nucleotides, from 6 to 8 nucleotides, or from 8 to 10 nucleotides, but may not be limited thereto.

In an embodiment of the present disclosure, the molecular barcode may be a base sequence prepared by randomly synthesizing the four bases of A, T, C and G, as illustrated in FIG. 1. For example, the random synthesis may mean that one of the bases of A, T, C and G does not have a 100% chance of being synthesized at a specific location.

In an embodiment of the present disclosure, the fixed sequence may be configured to distinguish the molecular barcode sequence that is a randomly synthesized base sequence and a DNA sequence to be analyzed that is not a molecular barcode. For example, the fixed sequence may be located between the molecular barcode and the DNA sequence to be analyzed and may consist of four identical nucleotide sequences for each sample, but may not be limited thereto.

In an embodiment of the present disclosure, the sample-unique sequence may have the same nucleotide sequence for each DNA fragment of each sample. Different DNA samples have different unique nucleotide sequences, and all DNA samples present in the same sample have the same sequence. Accordingly, all DNA fragments present in a sample have the same sequence, and, thus, when samples having different sample-unique sequences are mixed, it is possible to distinguish the samples.

In an embodiment of the present disclosure, the amplification product produced using the pair of primers may include an adaptor-complementary sequence, a sample-unique sequence, a molecular barcode and a fixed sequence in each of both flanking regions of the DNA fragment.

In an embodiment of the present disclosure, the amplification may be PCR amplification using the pair of primers, but may not be limited thereto. For example, the number of cycles for the amplification may be from 4 to 12, from 4 to 10, from 4 to 8, from 4 to 6, from 6 to 12, from 6 to 10, from 6 to 8, from 8 to 12, from 8 to 10, or from 10 to 12, but may not be limited thereto.

In an embodiment of the present disclosure, a specific DNA sequence (DNA with mutations) can be separated from the amplification product through the capture. The capture may be performed by hybridization, for example, solution-based hybridization, but may not be limited thereto. Some bases of the probe molecules may be biotinylated. The DNA fragment hybridized with a probe containing the biotinylated bases can be selectively separated using streptavidin-coated beads, but may not be limited thereto.

In an embodiment of the present disclosure, PCR amplification of normal DNA can be suppressed using the blocking oligonucleotide together with the nucleic acid probe during the hybridization. The blocking oligonucleotide is an oligonucleotide complementary to a base sequence of normal DNA and is bound to normal DNA at a higher efficiency than with DNA with mutations and suppresses PCR amplification of normal DNA.

Figure 2:
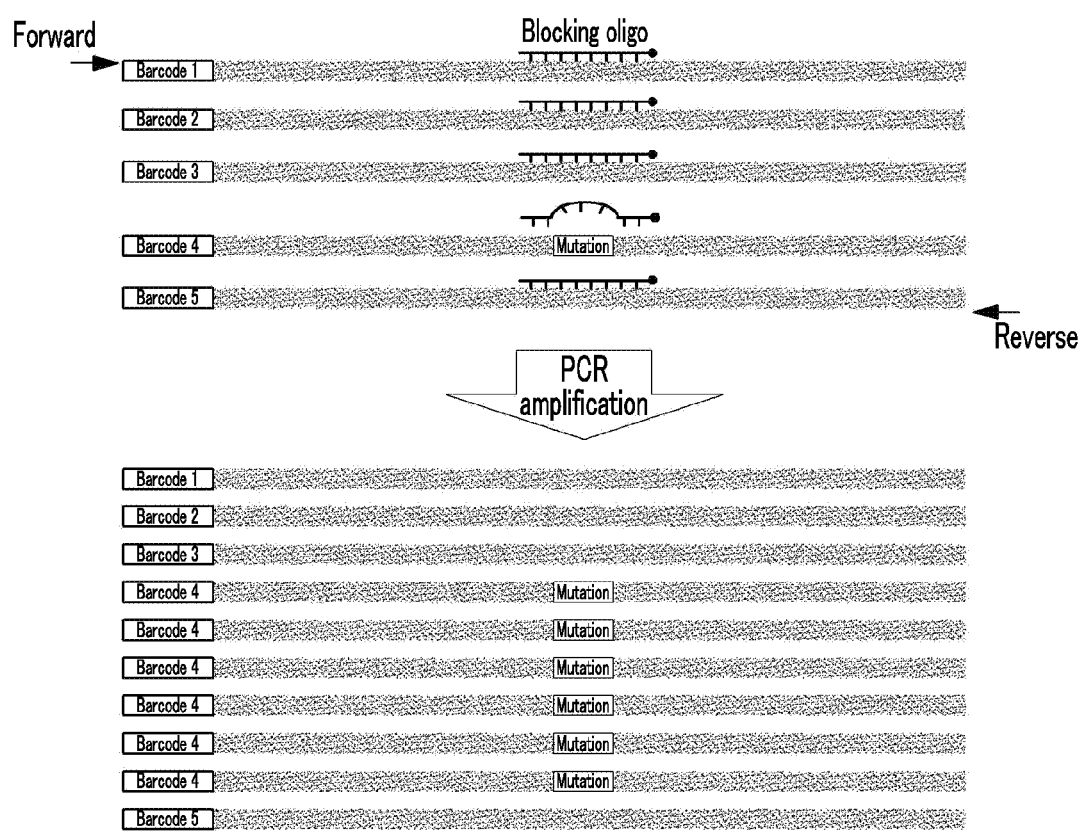
FIG. 2 is a schematic diagram illustrating the principle of a blocking oligonucleotide according to an embodiment of the present disclosure.
Figure 3:
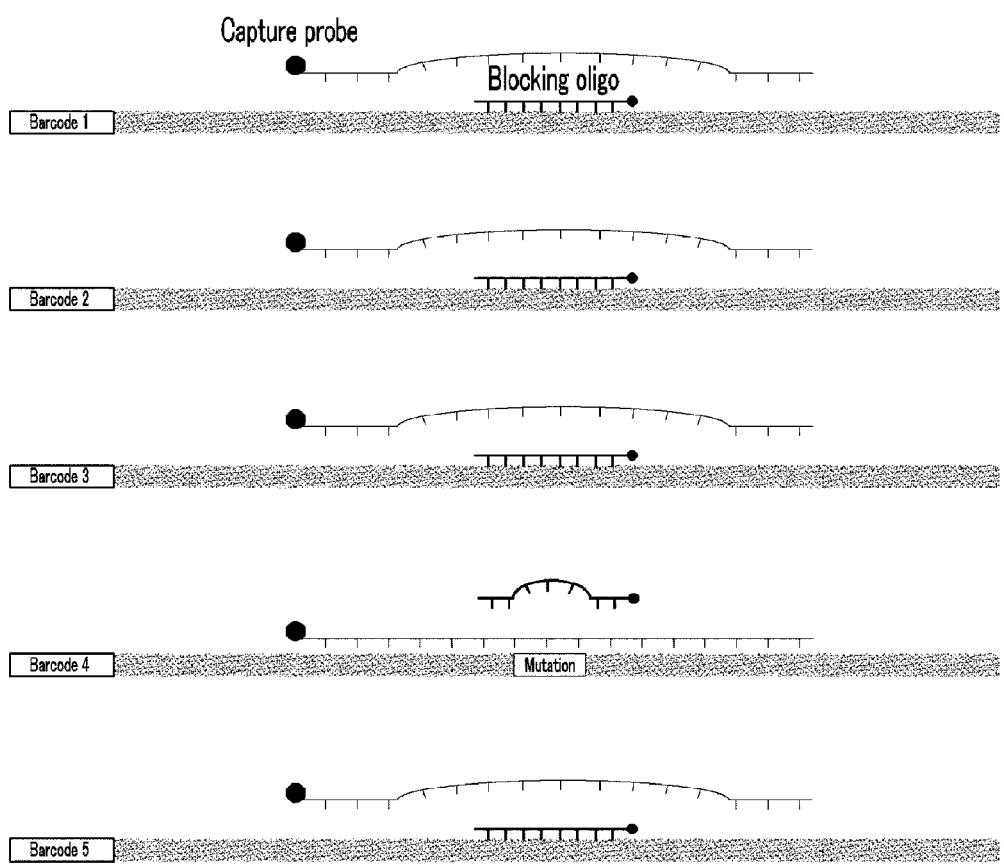
FIG. 3 is a schematic diagram illustrating a method for amplification and quantitation of a small amount of mutation using a molecular barcode and a blocking oligonucleotide according to an example of the present disclosure.

As illustrated in FIG. 1 and FIG. 2, the blocking oligonucleotide is complementary to a base sequence of normal DNA and thus can be bound to the normal DNA with high affinity. Therefore, the blocking oligonucleotide can suppress PCR amplification of the normal DNA. However, a base of the blocking oligonucleotide is not completely complementary to DNA with mutations (base mismatch), and, thus, the degree of binding between the blocking oligonucleotide and the DNA with mutations is relatively low. Accordingly, the DNA with mutations can be relatively well PCR-amplified compared to the normal DNA, and, thus, the ratio of the amount of PCR product of the normal DNA to the amount of PCR product of the DNA with mutations can be biased. However, by simultaneously using the molecular barcode and the blocking oligonucleotide, the molecular barcode and a target DNA base sequence are read together to calculate the number of molecular barcodes of a DNA strand including mutations and convert into the ratio of mutations. Therefore, it is possible to quantitatively measure the ratio of DNA with mutations in an original sample regardless of biased amplification caused by the blocking oligonucleotide.

In an embodiment of the present disclosure, the blocking oligonucleotide may be locked nucleic acid (LNA), peptide nucleic acid (PNA), or 3'-modified oligonucleotide, but may not be limited thereto.

In an embodiment of the present disclosure, the blocking oligonucleotide may consist of from 4 to 20 nucleotides, but may not be limited thereto. For example, the blocking oligonucleotide may consist of from 5 to 50 nucleotides, from 5 to 40 nucleotides, from 5 to 30 nucleotides, from 5 to 20 nucleotides, from 5 to 10 nucleotides, from 10 to 50 nucleotides, from 10 to 40 nucleotides, from 10 to 30 nucleotides, from 10 to 20 nucleotides, from 20 to 50 nucleotides, from 20 to 40 nucleotides, from 20 to 30 nucleotides, from 30 to 50 nucleotides, from 30 to 40 nucleotides, or from 40 to 50 nucleotides, but may not be limited thereto.

In an embodiment of the present disclosure, the hybridization may be performed at a temperature ranging from about 40° C. to about 95° C., but may not be limited thereto.

In an embodiment of the present disclosure, if the hybridization is performed at less than about 40° C., a double-stranded DNA fragment may not be separated into single strands and may not be complementarily bound to the blocking oligonucleotide, or although the DNA fragment is separated into single strands and bound to the blocking oligonucleotide, it is likely to be bound to not a specific DNA fragment, but a non-specific random DNA fragment. Therefore, the hybridization is performed at a temperature ranging desirably from about 40° C. to about 95° C.

In an embodiment of the present disclosure, if the hybridization is performed at more than about 95° C., only single-stranded DNA fragments are present. Since the single-stranded DNA cannot be bound to the blocking oligonucleotide, the hybridization is performed at a temperature ranging desirably from about 40° C. to about 95° C.

For example, the hybridization may be performed at a temperature ranging from about 40° C. to about 95° C., from about 40° C. to about 80° C., from about 40° C. to about 65° C., from about 40° C. to about 50° C., from about 50° C. to about 95° C., from about 50° C. to about 80° C., from about 50° C. to about 65° C., from about 65° C. to about 95° C., from about 65° C. to about 80° C., or from about 80° C. to about 95° C., but may not be limited thereto.

In an embodiment of the present disclosure, the hybridization may be performed in a range in which the concentration of the blocking oligonucleotide is from about 1 time to about 100 times the concentration of the probe, but may not be limited thereto.

In an embodiment of the present disclosure, if the concentration of the blocking oligonucleotide is less than about 1 time the concentration of the probe, a sufficient amount of blocking oligonucleotide is not present in the mixture, and, thus, the nucleic acid probe may not selectively capture the DNA strand including mutations. Also, if the concentration of the blocking oligonucleotide is more than about 100 times the concentration of the probe, a large amount of blocking oligonucleotide is present in the mixture, and, thus, the blocking oligonucleotide is bound to a DNA fragment in a competitive manner with the nucleic acid probe. Accordingly, DNA fragments in a corresponding region are less likely to be bound to the nucleic acid probe due to the blocking oligonucleotide, which may cause a decrease in capture rate efficiency. Therefore, the hybridization is performed in a range in which the concentration of the oligonucleotide is desirably from about 1 time to about 100 times the concentration of the probe.

For example, the concentration of the oligonucleotide may be from about 1 time to about 100 times, from about 1 time to about 50 times, from about 1 time to about 20 times, from about 1 time to about 10 times, from about 10 times to about 100 times, from about 10 times to about 50 times, from about 10 times to about 20 times, from about 20 times to about 100 times, from about 20 times to about 50 times, or from about 50 times to about 100 times the concentration of the probe, but may not be limited thereto.

In an embodiment of the present disclosure, the hybridization may be performed for from about 1 hour to about 24 hours, but may not be limited thereto. For example, if the hybridization is performed for less than 1 hour, there is not enough time for the nucleic acid probe, the blocking oligonucleotide, and the DNA fragment to be bound to each other, and, thus, a sufficient amount of captured product may not be obtained. Therefore, the hybridization is performed for desirably from about 1 hour to about 24 hours.

For example, the hybridization may be performed for about 1 hour to about 24 hours, from about 1 hour to about 20 hours, from about 1 hour to about 16 hours, from about 1 hour to about 12 hours, from about 1 hour to about 6 hours, from about 6 hours to about 24 hours, from about 6 hours to about 20 hours, from about 6 hours to about 16 hours, from about 6 hours to about 12 hours, from about 12 hours to about 24 hours, from about 12 hours to about 20 hours, from about 12 hours to about 16 hours, from about 16 hours to about 24 hours, from about 16 hours to about 20 hours, or from about 20 hours to about 24 hours, but may not be limited thereto.

In an embodiment of the present disclosure, the library for next-generation sequencing can be produced by amplifying the captured product using the common primer sequence.

In an embodiment of the present disclosure, the amplification of the captured product does not affect a molecular barcode present in the captured product. Therefore, a product produced in this process can be removed by analyzing the molecular barcode, but may not be limited thereto.

A second aspect of the present disclosure provides a method for detecting a small amount of mutation sequence using next-generation sequencing, including: performing next-generation sequencing of a library produced by the method according to the first aspect of the present disclosure; aligning, in a reference sequence, the library from which an adaptor-complementary sequence and a molecular barcode sequence are removed; re-ligating a molecular barcode to the aligned sequence; and performing sequencing of the re-ligated sequence.

Detailed descriptions of the detection method according to the second aspect of the present disclosure, which overlap with those of the first aspect of the present disclosure, are omitted hereinafter, but the descriptions of the first aspect of the present disclosure may be identically applied to the second aspect of the present disclosure, even though they are omitted hereinafter.

The method for detecting a small amount of mutation sequence can be described with reference to FIG. 4 and FIG. 5. First, next-generation sequencing is performed on a library produced by the method for producing a library. Then, during FASTQ filtration, an adaptor-complementary sequence and a molecular barcode sequence are removed from a data file produced by the next-generation sequencing. For example, if the same molecular barcode is identified in the plurality of amplification products, it is determined to be redundant and removed. If it is not removed, when there is an additional sequence other than a read sequence at the time of alignment in the reference sequence, it may be misaligned not in a specific region, but in a random region.

Then, the sequence from which the adaptor sequence and the molecular barcode sequence have been removed is aligned in the reference sequence. The reference sequence may be sequence information stored in a sequence database available in the art. The reads can be aligned using a sequence alignment tool known in the art or a tool for read alignment. Examples of the sequence alignment tool may include BWA, BarraCUDA, BBMap, BLASTN, Bowtie, NextGENe, or UGENE, but may not be limited thereto.

Then, a molecular barcode extracted during a sorting process is re-ligated to each DNA sequence using a sequence identifier assigned to the aligned sequence.

In an embodiment of the present disclosure, the reason for re-litigating the molecular barcode is to quantify the ratio of DNA with mutations in the original DNA sample. By calculating the ratio of the molecular barcode, the ratio of amplified mutations can be converted into the ratio of DNA with mutations before amplification. For example, if sequencing is performed without removing the molecular barcode, it may not be performed normally.

Finally, after re-ligation of the molecular barcode, the process of detecting a small amount of mutation sequence by sequencing may further include converting the ratio of a small amount of mutation sequence that changes before and after amplification according to bias caused by the blocking oligonucleotide by using the re-ligated molecular barcode.

In an embodiment of the present disclosure, the blocking oligonucleotide is complementary to a base sequence of normal DNA and thus can be bound to the normal DNA with high affinity. Therefore, the blocking oligonucleotide can suppress PCR amplification of the normal DNA. However, a base of the blocking oligonucleotide is not completely complementary to DNA with mutations (base mismatch), and, thus, the degree of binding between the blocking oligonucleotide and the DNA with mutations is relatively low. Accordingly, the DNA with mutations can be relatively well PCR-amplified compared to the normal DNA, and, thus, the ratio of the amount of PCR product of the normal DNA to the amount of PCR product of the DNA with mutations can be biased. However, by simultaneously using the molecular barcode and the blocking oligonucleotide, the molecular barcode and a target DNA base sequence are read together to calculate the number of molecular barcodes of a DNA strand including mutations and convert into the ratio of mutations. Therefore, it is possible to quantitatively measure the ratio of DNA with mutations in an original sample regardless of biased amplification caused by the blocking oligonucleotide.

Mode for Carrying Our the Invention

Hereinafter, the present disclosure will be explained in more detail with reference to Examples. However, the following Examples are illustrative only for better understanding of the present disclosure but do not limit the present disclosure.

EXAMPLES

Library Production

A library was produced to analyze the sequence of cell-free DNA through NGS using Horizon's cell-free DNA reference material.

The library was produced using the generic Illumina platform library kit. First, an end-repair process and an A-tailing process were performed to increase the unidirectional binding efficiency of adaptors that uniformly match both ends of DNA and are bound to a flowcell primer in NGS equipment, and an adaptor-ligation process was performed to bind adapters with a half sequence to both ends of DNA. The adaptor contained a molecular barcode consisting of eight random nucleotides in the DNA direction.

Then, PCR was performed to ligate a full adaptor based on the half-sequence adaptor (adaptor-complementary sequence) ligated to the both ends of the DNA. The full adaptor used a pair of primers consisting of an adaptor-complementary sequence for NGS, a sample-unique sequence, a molecular barcode, and a fixed sequence. In order to distinguish the molecular barcode and a DNA sequence to be analyzed, a fixed sequence consisting of four nucleotides was placed between the molecular barcode and the DNA.

A total of 50 µL of a mixed solution containing 20 µL of the DNA with the half-sequence adaptors, 2.5 µL of each of the primers and 25 µL of an amplification mixture (NG218-01) was reacted under the following conditions. After reaction at 98° C. for 2 minutes, a cycle consisting of 98° C. for 20 seconds, 65° C. for 30 seconds and 72° C. for 1 minute was repeated 6 to 10 times, followed by reaction at 72° C. for 10 minutes and storage at 4° C.

Then, in order to analyze only a specific DNA sequence of the DNA with the molecular barcode ligated thereto, DNA capture was performed by in-solution hybridization. The in-solution hybridization is a method for selecting only a specific DNA molecule by mixing a nucleic acid probe consisting of a nucleotide that can be complementarily bound to a specific DNA sequence with 1 ug of DNA with a molecular barcode ligated thereto.

First, a blocking oligonucleotide having a sequence complementary to a general sequence of a specific DNA to be screened was mixed with the nucleic acid probe to lower the screening efficiency of DNA with a common sequence and increase the screening efficiency of DNA with a mutation sequence. After the DNA with the molecular barcode was reacted at 95° C. for 10 minutes, the nucleic acid probe and the blocking oligonucleotide with a concentration 5 times the concentration of the nucleic acid probe were mixed and reacted at 65° C. for 4 hours. Then, after the reaction for 4 hours, the mixture was mixed with magnetic streptavidin beads and reacted at 65° C. for 45 minutes. The streptavidin beads were bound to specific molecules of the probe, thereby selecting specific DNA bound to the nucleic acid probe.

Then, the selected DNA was repeatedly washed at 65° C. and room temperature for purification. PCR was performed based on an adaptor-complementary sequence of the selected DNA. A total of 50 µL of a mixed solution containing 20 µL of the selected DNA, 5 µL of a mixed solution containing forward and reverse primers and 25 µL of an amplification mixture (NG218-01) was reacted under the following conditions. After reaction at 98° C. for 45 seconds, a cycle consisting of 98° C. for 15 seconds, 60° C. for 30 seconds and 72° C. for 1 minute was repeated 12 times, followed by reaction at 72° C. for 10 minutes and storage at 4° C. 75 µL of purification beads (DxSeq) was reacted with the amplified mixture to purify the amplified DNA (Example 1).

Library Production

In order to optimize the detection of mutations according to the hybridization conditions, libraries were produced in the same manner as the method for producing a library described in Example 1 except the reaction temperature, the concentration of blocking oligonucleotide, and the reaction time in a mixing and capture reaction between a capture probe and the blocking oligonucleotide. The hybridization temperature, the concentration of blocking oligonucleotide, and the hybridization time for each of Examples 2 to 11 are as shown in Tables 1 to 4 below.

Nucleic Acid Sequencing

The final product of in-solution hybridization and PCR was sequenced using Illumina's MiSeq instrument, and a FASTQ data file, which is raw data having base sequence information, was generated. The FASTQ data file contained all DNA molecular sequences, adaptor sequences and molecular barcode sequence information included in the final product.

Then, the adaptor sequences and the molecular barcode sequences were removed from all the sequences in the FASTQ, and the DNA molecular sequences were aligned in the human reference genome. After the alignment, the molecular barcode sequences were re-ligated using sequence identifiers assigned to the respective DNA sequences.

Figure 4:
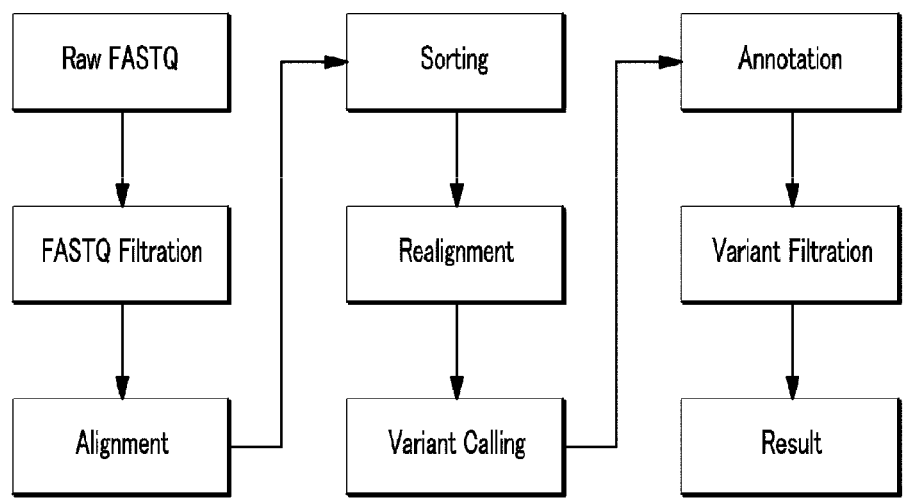
FIG. 4 is a flowchart showing an analysis process of next-generation sequencing data according to an example of the present disclosure.
Figure 5:
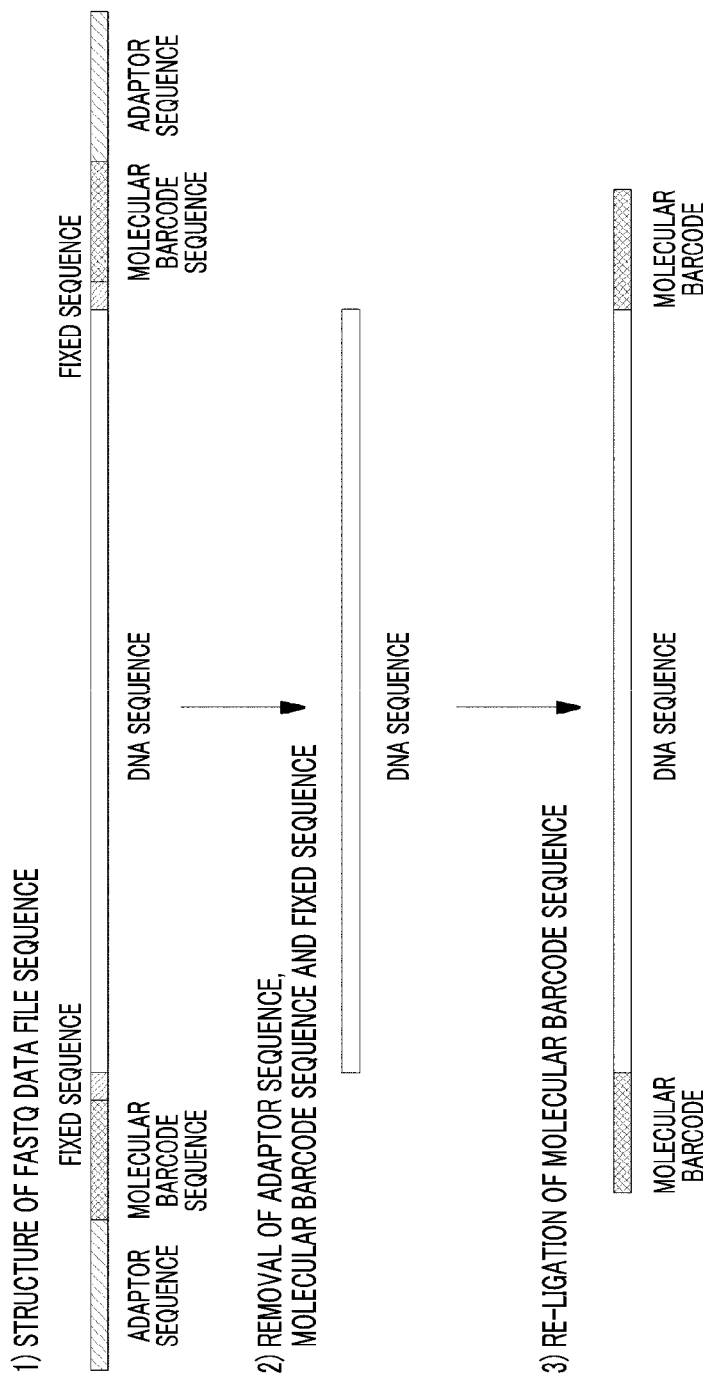
FIG. 5 is a schematic diagram illustrating a process of extracting and re-ligating a molecular barcode from and to next-generation sequencing data according to an example of the present disclosure.

Thereafter, variant calling was performed to confirm the type and ratio of mutations present in the DNA sequence (FIG. 4).

The ratio of DNA with mutations was different from that before amplification due to bias caused by the blocking oligonucleotide, which was converted into the ratio of mutations before amplification by using the re-ligated molecular barcode.

Figure 6:
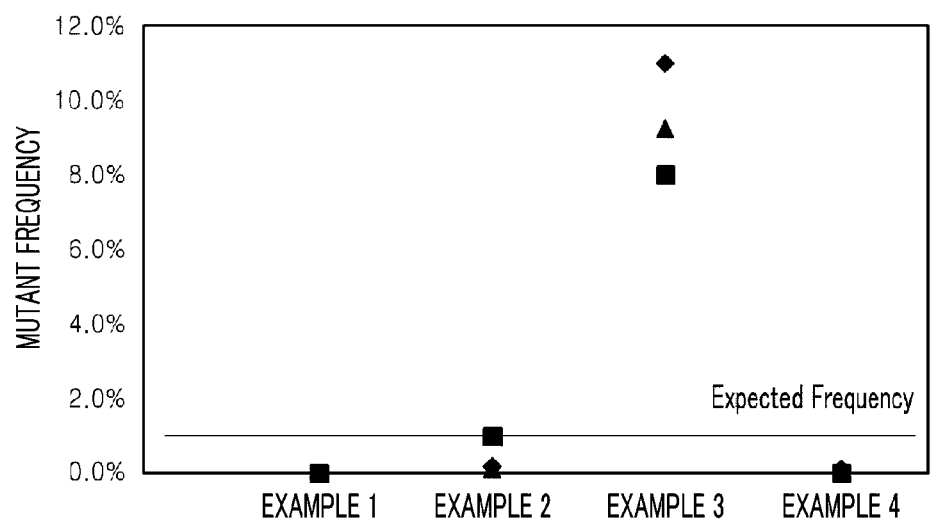
FIG. 6 is a graph showing the mutation detection frequency depending on the concentration of a blocking oligonucleotide under the same hybridization temperature and the same hybridization time according to an example of the present disclosure (♦: KRAS-G12D, ■: PIK3CA E545K, ▲: TP53 R175H).

FIG. 6 and Table 1 are graphs showing the mutation detection frequency depending on the concentration (multiples) of a blocking oligonucleotide relative to a probe under the same hybridization temperature and the same hybridization time (allele frequency 1%, ♦: KRAS-G12D, ■: PIK3CA E545K, ▲: TP53 R175H).

TABLE 1

| Condition | Temperature (° C.) | Concentration (Multiples of blocking oligonucleotide relative to probe) | Time (hr) |
| --- | --- | --- | --- |
| Example 1 | 65 | 0 | 4 |
| Example 2 | 65 | 1 | 4 |
| Example 3 | 65 | 10 | 4 |
| Example 4 | 65 | 100 | 4 |

As shown in FIG. 6 and Table 1, the capture reaction in which the DNA with the molecular barcode ligated thereto was mixed with the nucleic acid probe and the blocking oligonucleotide was performed at 65° C. for 4 hours and the concentration of the blocking oligonucleotide was 0 time (Example 1), 1 time (Example 2), 10 times (Example 3), and 100 times (Example 4) the concentration of the probe, and the mutation frequency was the highest in Example 3.

Figure 7:
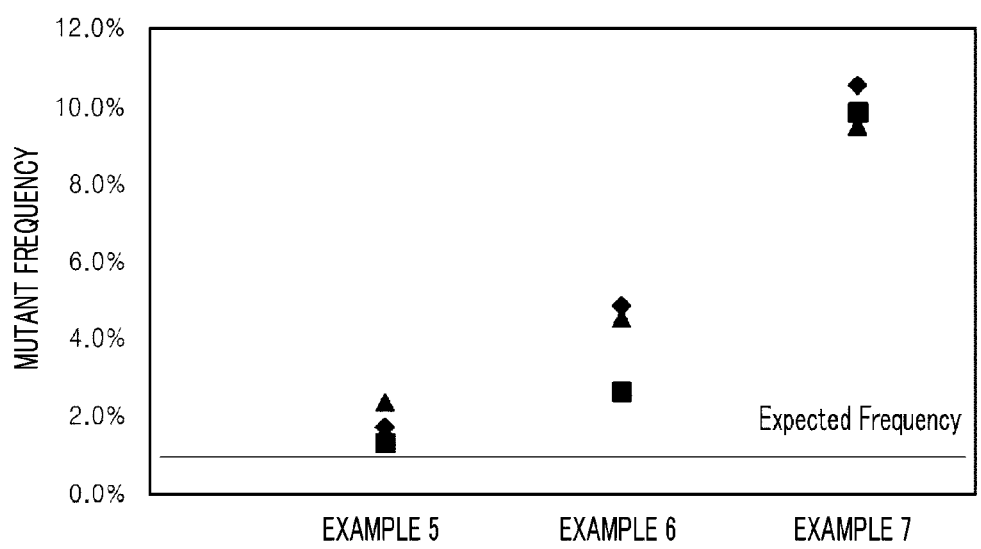
FIG. 7 is a graph showing the mutation detection frequency depending on the hybridization temperature under the same hybridization time and the same concentration of a blocking oligonucleotide according to an example of the present disclosure (♦: KRAS-G12D, ■: PIK3CA E545K, ▲: TP53 R175H).

FIG. 7 and Table 2 are graphs showing the mutation detection frequency depending on the hybridization temperature under the same hybridization time and the same concentration of a blocking oligonucleotide (allele frequency 1%, ♦: KRAS-G12D, ■: PIK3CA E545K, ▲: TP53 R175H).

TABLE 2

| Condition | Temperature (° C.) | Concentration (Multiples of blocking oligonucleotide relative to probe) | Time (hr) |
|---|---|---|---|
| Example 5 | 57 | 10 | 4 |
| Example 6 | 61 | 10 | 4 |
| Example 7 | 65 | 10 | 4 |

As shown in FIG. 7 and Table 2, the capture reaction in which the DNA with the molecular barcode ligated thereto was mixed with the nucleic acid probe and the blocking oligonucleotide was performed at 65° C. for 4 hours, and the mutation frequency was the highest in Example 7 in which the concentration of the blocking oligonucleotide was 10 times the concentration of the probe.

Figure 8:
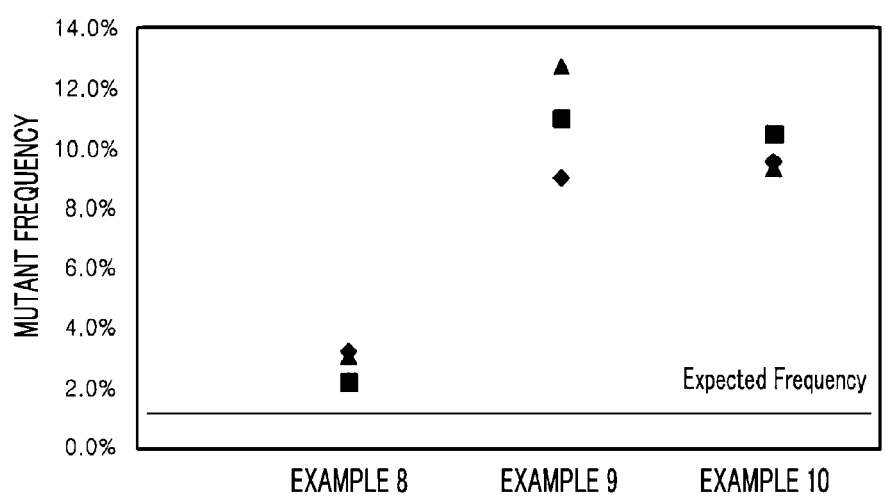
FIG. 8 is a graph showing the mutation detection frequency depending on the hybridization time under the same hybridization temperature and the same concentration of a blocking oligonucleotide according to an example of the present disclosure (♦: KRAS-G12D, ■: PIK3CA E545K, ▲: TP53 R175H).

FIG. 8 and Table 3 are graphs showing the mutation detection frequency depending on the hybridization time under the same hybridization temperature and the same concentration of a blocking oligonucleotide (allele frequency, ♦: KRAS-G12D, ■: PIK3CA E545K, ☆: TP53 R175H).

TABLE 3

| Condition | Temperature (° C.) | Concentration (Multiples of blocking oligonucleotide relative to probe) | Time (hr) |
|---|---|---|---|
| Example 8 | 65 | 10 | 2 |
| Example 9 | 65 | 10 | 4 |
| Example 10 | 65 | 10 | 6 |

As shown in FIG. 8 and Table 3, it can be seen that although the mutation frequency increases with the hybridization time, it is maintained at a constant level after 4 hours.

Table 4 is a graph showing the mutation detection frequency depending on the concentration of the blocking oligonucleotide relative to the concentration of the probe (allele frequency: 1%). As shown in the following Table 4, it can be seen that when the concentration of the blocking oligonucleotide was 5 times higher than that of the probe, the allele frequency increased 13 to 17 times.

TABLE 4

| Condition | Temperature (° C.) | Concentration (Multiples of blocking oligonucleotide relative to probe) |
|---|---|---|
| Example 11 | 65 | 10 |

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

I claim:

1. A method for producing a library for next-generation sequencing, comprising:
   ligating an adaptor to both ends of a target double-stranded DNA fragment to obtain an adaptor-ligated DNA fragment;
   providing a pair of primers for amplifying the adaptor-ligated DNA fragment;
   producing an amplification product containing a molecular barcode by amplifying the adaptor-ligated DNA fragment using the pair of primers;
   capturing a specific DNA sequence to be selected from the amplification product containing the molecular barcode by hybridization with a capture probe and a blocking oligonucleotide to obtain a captured product; and
   amplifying the captured product using a common primer sequence,
   wherein each of the pair of primers for amplifying the adaptor-ligated DNA fragment comprises:
   i) an adaptor-complementary sequence having a nucleotide sequence complementary to the adaptor,
   ii) a sample-unique sequence having the same nucleotide sequence for each DNA fragment,
   iii) the molecular barcode having a nucleotide sequence unique to each DNA fragment, and
   iv) a fixed sequence for distinguishing the molecular barcode and a DNA sequence,
   wherein the blocking oligonucleotide has a sequence complementary to a wild-type of specific DNA sequence to be selected from DNA fragments.

2. The method for producing a library for next-generation sequencing of claim 1, wherein the molecular barcode consists of from 4 to 10 nucleotides.

3. The method for producing a library for next-generation sequencing of claim 1, wherein the blocking oligonucleotide consists of from 15 to 20 nucleotides.

4. The method for producing a library for next-generation sequencing of claim 1, wherein the blocking oligonucleotide is locked nucleic acid (LNA), peptide nucleic acid (PNA), or 3'-modified oligonucleotide.

5. The method for producing a library for next-generation sequencing of claim 4, wherein the hybridization is performed at a temperature ranging from 40° C. to 95° C.

6. The method for producing a library for next-generation sequencing of claim 1, wherein the number of cycles for the amplification using the pair of primers for amplifying the adaptor-ligated DNA fragment is from 4 to 12.

7. The method for producing a library for next-generation sequencing of claim 1, wherein the hybridization is performed in a range in which the concentration of the blocking oligonucleotide is from 1 time to 100 times the concentration of the probe.

8. The method for producing a library for next-generation sequencing of claim 1, wherein the hybridization is performed for from 1 hour to 24 hours.

* * * * *

SEQUENCE LISTING

```
<160> NUMBER OF SEQ ID NOS: 3

<210> SEQ ID NO 1
<211> LENGTH: 82
<212> TYPE: DNA
<213> ORGANISM: Artificial Sequence
<220> FEATURE:
<223> OTHER INFORMATION: Forward primer including molecular barcode
<220> FEATURE:
<221> NAME/KEY: primer_bind
<222> LOCATION: (71)..(78)
<223> OTHER INFORMATION: "n" is any nucleotide ("a", "g", "c" or "t/u")

<400> SEQUENCE: 1
aatgatacgg cgaccaccga gatctacaca ttactcgaca ctctttccct acacgacgct    60
cttccgatct nnnnnnnngt ca                                              82

<210> SEQ ID NO 2
<211> LENGTH: 78
<212> TYPE: DNA
<213> ORGANISM: Artificial Sequence
<220> FEATURE:
<223> OTHER INFORMATION: Reverse primer
<220> FEATURE:
<221> NAME/KEY: primer_bind
<222> LOCATION: (67)..(74)
<223> OTHER INFORMATION: "n" is any nucleotide ("a", "g", "c" or "t/u")

<400> SEQUENCE: 2
```

```
caagcagaag acggcatacg agattatagc ctgtgactgg agttcagacg tgtgctcttc        60
cgatctnnnn nnnngtca                                                     78

<210> SEQ ID NO 3
<211> LENGTH: 18
<212> TYPE: DNA
<213> ORGANISM: Artificial Sequence
<220> FEATURE:
<223> OTHER INFORMATION: blocking oligonucleotide

<400> SEQUENCE: 3
gttggagctg gtggcgta                                                     18
```